United States Patent
Modzelewski et al.

(10) Patent No.: US 9,766,222 B2
(45) Date of Patent: Sep. 19, 2017

(54) METERS WITH CHANGEABLE MODULES

(71) Applicant: Trividia Health, Inc., Ft. Lauderdale, FL (US)

(72) Inventors: Brent E. Modzelewski, Boca Raton, FL (US); George R. Rounds, Parkland, FL (US)

(73) Assignee: Trividia Health, Inc., Ft. Lauderdale, FL (US)

( * ) Notice: Subject to any disclaimer, the term of this patent is extended or adjusted under 35 U.S.C. 154(b) by 373 days.

(21) Appl. No.: 14/206,143

(22) Filed: Mar. 12, 2014

(65) Prior Publication Data

US 2014/0260568 A1    Sep. 18, 2014

Related U.S. Application Data

(60) Provisional application No. 61/783,166, filed on Mar. 14, 2013.

(51) Int. Cl.
    *G01N 33/48* (2006.01)
    *G01N 33/66* (2006.01)
    *G01N 33/487* (2006.01)

(52) U.S. Cl.
    CPC ....... *G01N 33/48* (2013.01); *G01N 33/48785* (2013.01); *G01N 33/66* (2013.01)

(58) Field of Classification Search
    CPC ................ G01N 33/48; G01N 33/48785
    See application file for complete search history.

(56) References Cited

U.S. PATENT DOCUMENTS

| 8,394,328 | B2 | 3/2013 | Neel et al. | |
|---|---|---|---|---|
| 9,263,775 | B1 * | 2/2016 | Lowchareonkul | H01M 10/425 |
| 2004/0249999 | A1 * | 12/2004 | Connolly | A61B 5/0002 |
| | | | | 710/33 |
| 2005/0009126 | A1 | 1/2005 | Andrews et al. | |
| 2006/0189895 | A1 * | 8/2006 | Neel | A61B 5/1411 |
| | | | | 600/584 |
| 2007/0071538 | A1 * | 3/2007 | Doria | A45D 34/041 |
| | | | | 401/219 |
| 2010/0087754 | A1 * | 4/2010 | Rush | A61B 5/1411 |
| | | | | 600/583 |

(Continued)

FOREIGN PATENT DOCUMENTS

| EP | 2394577 | 12/2011 |
|---|---|---|
| WO | 2009/027950 | 3/2009 |

OTHER PUBLICATIONS

Tenderich, Amy, "WaveSense Jazz Meter to Connect with the iPhone", Jul. 6, 2010, http://www.healthline.com/diabetesmine/apple-clears-wavesense-jazz-meter-to-connect-with-the-iphone#2.*

(Continued)

*Primary Examiner* — Paul West
(74) *Attorney, Agent, or Firm* — Greenberg Traurig, LLP; David J. Dykeman; Roman Fayerberg (57) ABSTRACT

A customizable diagnostic meter is provided. The diagnostic meter includes a meter for performing a diagnostic test, wherein the meter includes a housing having a slot, and a module having one or more functions. The slot is configured to receive and removably secure at least a portion of the module. A customizable diagnostic meter kit including two or more modules configured to be inserted in a meter is also provided.

21 Claims, 10 Drawing Sheets

(56) References Cited

U.S. PATENT DOCUMENTS

2010/0249530 A1    9/2010   Rankers et al.
2010/0331645 A1   12/2010   Simpson et al.

OTHER PUBLICATIONS

"iTeck Dock Extender Converter 30-Pin Pass Through Adapter for iPhone 4, iPod & iPad 2", advertisement with review, Jan. 5, 2012.*
Provo, Frank, "Review: WaveSense Jazz blood sugar meter" Sep. 7, 2009.*
Dolan, Brian, "FDA promises regulatory guidance this year" Sep. 2010.*
PCT International Search Report based on PCT/US2014/024681 dated Jul. 25, 2014.
Extended European Search Report issued is European Application No. 14773314.1 dated Sep. 12, 2016.

\* cited by examiner

METERS WITH CHANGEABLE MODULES

RELATED APPLICATIONS

This application claims priority to and the benefit of Provisional Patent Application No. 61/783,166, filed Mar. 14, 2013, the contents of which are hereby incorporated herein by reference.

FIELD

The embodiments disclosed herein relate to diagnostic meters, and particularly to customizable diagnostic meters with user changeable modules.

BACKGROUND

Diagnostic testing systems are commonly used to perform various assays on various types of samples including medical and non-medical samples. A user of a diagnostic testing system must manage and carry not only the meter which may be bulky, but also a supply of test media and a sampling system such as a lancet set which are cumbersome to carry and may become separated from each other.

Also, diagnostic meters are often costly, inconvenient, and complex to use. Often a user will need or desire to use other devices or features in connection with the meter. It would be difficult and costly to upgrade to a new diagnostic meter having the desired features. A new meter may be more complex and larger. Separate devices with the desired features will also be complex as well as costly and cumbersome to carry.

It would be desirable to be able to extend the feature set of a diagnostic meter without unduly adding cost or complexity to the base meter.

SUMMARY

In an embodiment, a customizable diagnostic meter is provided. The customizable diagnostic meter includes a meter, such as a portable meter for performing a diagnostic test. The meter includes a housing having at least one slot, and a module having one or more functions. The slot is configured to receive and removably secure at least a portion of a module.

The meter may be a blood glucose meter. The module may be a passive module, an active module, or a combination of the two. The module may be a portable vial, a lancing device, a USB module, a wireless connection module, an audio module, a backlight module, a flashlight, a carbohydrate counter, an insulin bolus calculator, a scanner, or a combination thereof. The wireless connection module may include a Bluetooth or WiFi connection.

The meter may further include a module extender connected to the module. The module extender includes one or more features such as a flashlight and a backlight. The module may be a multi-function module such as a module including a carbohydrate counter and a scanner.

In an embodiment, a customizable diagnostic meter includes a meter, such as a portable meter, for performing a diagnostic test, wherein the meter includes a housing having at least one slot. The diagnostic meter also includes a first module having one or more functions, wherein the slot is configured to receive and removably secure at least a portion of the first module; and a second module having one or more functions, wherein the second module is configured for removable attachment to at least a portion of the first module. The first module may be different than the second module. The first module and/or the second module may include a portable vial, a lancing device, a USB module, a wireless connection module, an audio module, a backlight module, a flashlight, a carbohydrate counter, an insulin bolus calculator, a scanner, or a combination thereof.

In an embodiment, a customizable diagnostic meter kit is provided. The kit includes a meter for performing a diagnostic test, wherein the meter includes a housing having at least one slot. The kit also includes two or more modules, wherein each module has one or more functions and a portion that is configured to be inserted and removably secured in the slot. The portions of the two or more modules configured for insertion in the slot may be of the same size and shape. At least one of the module may be a portable vial, a lancing device, a USB module, a wireless connection module, an audio module, a backlight module, a flashlight, a carbohydrate counter, an insulin bolus calculator, a scanner, or a combination thereof. One module may be a USB module, and the kit may further include a USB cable.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Customizable diagnostic meters configured to receive user changeable modules, and modular meter systems and kits including such meters and modules are provided herein. The customizable diagnostic meter includes a meter for performing a diagnostic test and a module.

The meter may be a diagnostic meter used to perform various assays on various types of samples. The diagnostic test may be a qualitative or quantitative test to determine the presence, concentration or amount of one or more analytes in a sample. The analyte may be a medical analyte (such as glucose, ketones, cholesterol, triglycerides, human choriogonadotropin (HCG), hemoglobin HbA1c, fructosamine, carbohydrates, tumor markers, lead, anti-epilepsy drugs, bilirubin, liver function markers, toxins or their metabolites, controlled substances, blood coagulation factors (PT, ATPP), and others) contained in a biological sample (such as blood, urine, tissue, saliva, and others). However the diagnostic test is not limited to the medical field. Diagnostic test meters can also be used to monitor analytes or chemical parameters in non-medical samples such as water, food products, soil, sewage, sand, air, or any other suitable sample.

The meter is designed to perform a diagnostic test. For example, the meter may be designed to determine the amount of glucose in a sample of whole blood applied to a sample chamber of a test strip. The meter may employ a variety of techniques to perform a diagnostic test. For example, the meter may perform an electrochemical technique, such as for blood glucose testing.

The meter is customizable to include user selected features. In an embodiment, the meter is portable. In an embodiment, the meter can be used as a stand-alone meter. The meter may be of any suitable dimensions. The dimensions of the meter may be a size and shape that can accommodate a desired module of any size and shape. For example, the meter may be dimensioned to accommodate a module having a rounded, oval, elliptical, cylindrical, rectangular, or square shape, or a combination of those shapes. In an embodiment, the module is a portable vial having an oval or elliptical shape. In an embodiment, a meter may be about 70 mm in length and 50 mm in width. The dimensions of the meter may also be smaller such as about 40 mm in length by about 25 mm in width.

The meter includes a housing. The housing may be of any suitable dimensions to contain the electronic components of the meter. In an embodiment, the housing has a first end and a second end and a sidewall connecting the first end and the second end. In an embodiment, the sidewall of the housing has an oval or round shaped diameter. In an embodiment, the housing may have a flat first end and a flat second end. In an embodiment, the sidewall of the housing has an oval or round shaped diameter with a generally flat side. In an embodiment, the housing has a rectangular or square shaped cross-section. The housing may have any desired shape. For example, a housing may have a rounded shape such as an elliptical, cylindrical, or oval shape, or a square or rectangular shape. The housing may have sides of different sizes. The housing may have a portion that is tapered.

The housing has at least one slot. The slot is configured to receive and removably secure a module having one or more features or functions. Thus, the slot may be an opening of any width and depth that will receive at least a portion of a module. In an embodiment, the module is configured to slide into the slot and remain in mating engagement with the meter until removed by a user. In an embodiment, at least a portion of a module slides into the slot. In an embodiment, more than half of the module is insertable into the slot. In an embodiment, the module, when inserted and secured in the slot, protrudes from the slot. The module may be fully inserted in the slot such that one end of the module is exposed when the module is secured in the slot. In an embodiment, a substantial portion of the module is insertable into the slot.

The slot may be located anywhere in the housing. In an embodiment, the slot is located at the top of the housing. However, the slot may be positioned on a side or bottom of the housing. The module may be inserted into the meter from any side at any angle. Also, the slot may be centrally placed on a side of the module, or positioned off-center on a side of the module. In an embodiment, the slot may be placed closer to an edge of a side of the module. In an embodiment, the opening of the slot has dimensions that are suitable for receiving a module. In an embodiment, the length and the width of the opening of the slot are more than half the length and the width of the side of the module on which the slot is positioned. In an embodiment, the length and the width of the opening of the slot are less than half the length and the width of the side of the module on which the slot is positioned. The module may be inserted and secured in the meter for easy carrying.

Figure 1A:
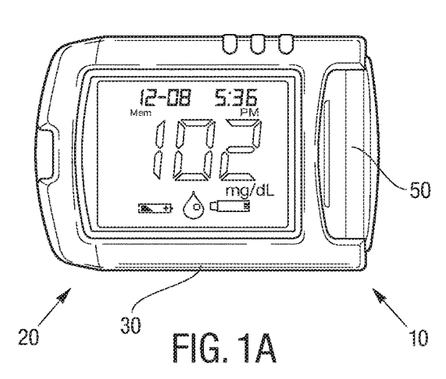
FIG. 1A is a plan view of an embodiment of a diagnostic meter having a module inserted therein.
Figure 1B:
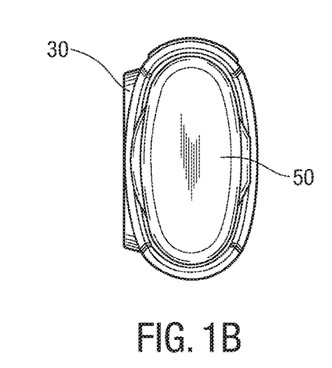
FIG. 1B is a top view of having the module of FIG. 1A.
Figures 1C, 1D:
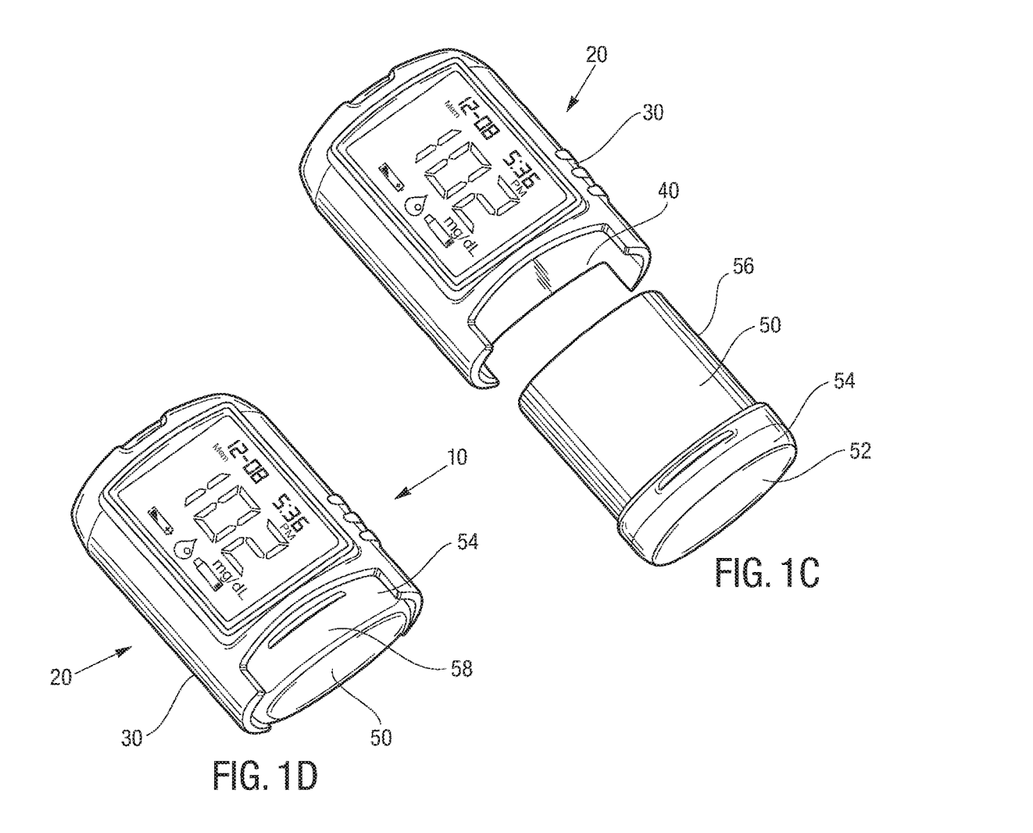
FIG. 1C is a perspective view of a meter and a module, wherein the module is a portable vial.
FIG. 1D is a perspective view of the meter of FIG. 1C with the portable vial inserted therein.

FIGS. 1A, 1B, 1C, and 1D show various views of an embodiment of customizable diagnostic meter 10 including a meter 20 including a housing 30 having a slot 40, and a module 50 configured for insertion in the slot 40. In the embodiment shown in FIGS. 1A, 1B, 1C, and 1D, the module 50 is a portable vial. FIG. 1A shows a plan view of an embodiment of a meter 20 having a module 50 inserted in the meter 20. FIG. 1B is a top view of the module 50 of FIG. 1A. FIG. 1C is a perspective view of the meter 20 and the module 50, and FIG. 1D is a perspective view of the meter 20 of FIG. 1C with a module 50 inserted therein. The modules may be sized and dimensioned to be inserted in the slot 40. The slot may be of any suitable dimensions.

The module inserted in the slot in the meter may also be of any suitable dimensions. In an embodiment, a module inserted in the meter as shown in FIG. 1B may be about 28 mm in width. The length of the module may vary. For example, the module may be about 10 mm to about 20 mm in length depending on the module. The meter and slot size need only be as large or small as to accommodate the largest desired module. In an embodiment, the meter is a small portable device and the size can vary according to implementation and desired modules.

The module may include 2, 3, 4, or more sections. In one embodiment, the module includes an outer section, a middle section, and an inner section. The outer section is generally the top surface that is exposed or protruding from the slot when the module is inserted into the meter. The outer section may be of any suitable dimensions. The outer section may have the same length and/or width as the meter. The outer section may have different lengths and/or widths than the meter. The inner section is the portion of the module that is fully inserted into the meter and does not extend beyond or outside the meter, and is not exposed when the module is in the meter. The middle section is the portion connecting the outer section and the inner section. The middle section may include a portion that is exposed and extends beyond the meter when the module is inserted in the meter, or the middle section may be fully inserted into the meter. The exposed middle portion of the module may be used to grip the module to insert the module in the meter and remove the module from the meter. Such gripping section of the middle section may have any suitable dimensions. In an embodiment, the length and width of the outer section is greater than the length and width of the middle section. In an embodiment, the length and width of the middle section is greater than the length and width of the inner section.

The module may be formed as a single unit or different sections of the module may be formed separately and then attached together. The module sections, such as the outer section, middle section, and inner section, may be of various lengths and widths so that the module has sections of varying sizes. The diameters of each section may be the same or different. For example, the outer section may have a slightly larger diameter than the middle section. Also, the middle section may have a slightly larger diameter than the inner section. In another embodiment, the outer section and the middle section may have the same diameter and the inner section may have a different diameter that is greater than or less than the diameter of the outer section and the inner section. The outer section may have a lip that mates with the meter to lock the module in the meter.

FIG. 1C shows an embodiment of a module 50 having an outer section 42, a middle section 54, and an inner section 56. FIG. 1D shows a module 50 having an exposed portion of the middle section 54 that may be used as a gripping section 58 by a user to remove the module 50 from the meter 20 and insert the module 50 into the meter 20.

The module may be secured in the slot using any suitable mechanism. For example, the module may be snapped into the meter. In an embodiment, the module may snap into the meter with a passive detent, snap ring or with a push button release. The module may slide into the meter and be held by a slide locking feature. In an embodiment, the meter may slide into the meter and be held by electrical components such as a card edge connector, DB9, or header.

The module or the meter may include a latch that is releasable. In an embodiment, the module may be secured using a latch and release system. In an embodiment, the module may slide into the meter and be held with a push to release latch such as an SD card holder or a cabinet latch. The module may also slide into the meter and be held by an elastomeric feature such as a friction fit. The meter or the module may include a locking feature to secure the module to the meter. In an embodiment, the meter and the module may be held by magnetic force, or by evacuation of air as in a suction cup, mechanical fastening, or other mechanical connections. Accordingly, the meter or module may have various mechanisms to removably secure the module to the meter.

The slot 40 may include a cutaway portion such that the slot 40 is formed on one side of the housing 30 of a meter 20 and also includes a portion cut away on another side of the housing 30 of a meter 20 (see, for example, meter 20 of FIGS. 1A, 1B, 1C, and 1D).

A diagnostics meter having a housing 30 with one or more slots 40 is configured to accept at least a portion of one or more modules 50 having one or more features or functions. Modules are used to extend the feature set of the meter without unduly adding cost or complexity to the base meter model. The cost and complexity of the feature is often incurred in the module itself. Additionally, users can select which features they want by purchasing and utilizing the module(s) of their choice.

The modules described herein include both passive modules and active modules that are hot swappable by the end user. Generally, passive modules are modules that are primarily mechanical in nature and do not contain electronics. Passive modules include, but are not limited to, a container for test strip storage or lancet storage and a lancing device with a space for lancet storage and/or disposal. Other passive modules include, for example, modules that contain hand sanitizer, paper logbook and/or pen, a medicine bottle, a glucose tablet bottle, rain/water cover (pull out and zip, similar to a hidden hood on a jacket), and any other modules having mechanical features that may be contained within the module and inserted into a slot in a meter.

In general, active modules are modules that include internal electronics with or without their own power supply. Active modules include, for example, a flashlight. A flashlight may be used for illuminating the patient's testing equipment in low light conditions. Other active modules include modules for wireless or wired connectivity including, but not limited to, Bluetooth/Bluetooth Low Energy, WiFi, Zigbee, USB, Ethernet, serial/RS-232, memory card/storage (mass storage device), GSM modem (or similar cellular phone connection), and other modules that can be used to establish a wireless or wired connection. For example, an active module can obtain a key (e.g., a private key) for use in communication with a computing device. The module can obtain the key by, for example, generating the private key (e.g., via a random or pseudorandom key generator), receiving the private key as input from a user, and/or reading the private key (e.g., via a scanning mechanism). In one embodiment, the active module can then pair with the computing device via a wireless communication medium, such as radio frequency (RF), such as WiFi, Bluetooth®, Bluetooth Smart®, ANT/ANT+®, ZigBee®, cellular, Near Field Communication (NFC), optical (e.g., barcode, IRDA, OCR, or similar devices), sound (e.g., ultrasonic, subsonic/ vibratory, or similar sounds), magnetic, thermal, electrical (e.g., resistance, impedance, voltage, current) or similar channels. The active module can then finalize the pairing with the computing device.

Active modules may also include talking or audio modules to announce the blood glucose value to the user, as well as instruct a user through the testing process. Other active modules include, but are not limited to, modules with their own display, such as a carbohydrate counting module with buttons and a small LCD to show the total carbohydrates, scanners such as bar code scanners (to read strip lot codes or patient identification and import carbohydrate or other nutritional information from food packages), activity monitors (pedometers or other accelerometer type activity monitors), a calorie counter, an insulin pump controller, an insulin/carbohydrate calculator, a pulse oximeter (to check pulse and oxygenation), an emergency beacon/alert, a GPS, a Peak Flow meter, an additional analyte test adapter (cholesterol, ketone, HbA1c, Liver Enzyme, hematocrit, anemia, cardiac marker), and any other desired features using electronics.

In an embodiment, the active module may use its own battery rather than relying on the meter battery. In an embodiment, the active module has its own battery and can function when not inserted in the module.

Also, the active modules may include a LED light or other indicator to show use of one or more features of the active module. Active modules may also include a button to activate a function of the active module. If an active module includes more than one feature or function, then the active module may include one or more buttons for controlling those features or functions.

FIGS. 1A-3B show embodiments of diagnostic meters including passive modules.

FIGS. 1A, 1B, 1C, and 1D show embodiments of a meter 20 and a portable vial as discussed above. FIG. 1A is a plan view of the meter 20 with the module 50 or portable vial inserted in the meter 20. FIG. 1B shows a top view of the module 50 inserted into the meter. FIG. 1C is a perspective view of the meter and the module. FIG. 1D is a perspective view of the meter 20 of FIG. 1C with the portable vial inserted therein.

A container or vial that holds test strips may be a module that can be inserted into the meter. The container can be opened and the strips accessed without removing the vial from the meter.

Figure 2A:
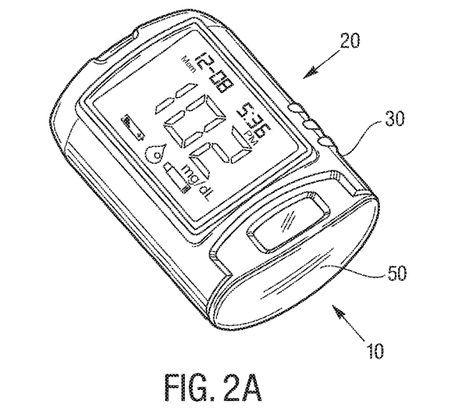
FIG. 2A is a perspective view of a meter and a module inserted therein, wherein the module is a lancing device module.
Figure 2B:
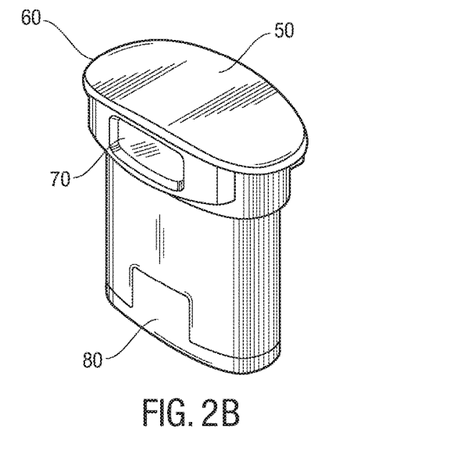
FIG. 2B is a perspective view of the lancing device module of FIG. 2A.

FIG. 2A is a perspective view of a meter 20 and a module 50 inserted therein, wherein the module 50 is a lancing device module. FIG. 2B is a perspective view of the lancing device module of FIG. 2A. The lancing device module shown in FIG. 2B functions as a lancing device and can be inserted into the meter 20. The lancing device module may be configured to function while inserted in the meter 20 or the lancing device module may be removed for use. In an embodiment, the lancing device module includes an arm 60 that may be pulled back. The lancing device generally includes a mechanism for propelling a lancet from the device and through skin to a depth selected by the user. Also, the lancing device module may include a button 70 to fire or trigger the lancet. The lancing device module may also include a lancet storage area and depth setting adjustment 80. The lancing device may provide extra lancet storage inside the module 50. The lancing device may be used for an arm or a finger. In an embodiment, the module may include any other sampling device suitable for obtaining a sample to be tested.

In an embodiment, a passive module may include two or more features or functions. Such passive modules may be a split module where the module includes two or more parts and each part has a feature or function that may be the same or different. The different parts of the split module may be the same size and shape or be of different sizes and shapes. Also, the different parts of a split module may be integrated to form a single unit, or the different parts may be separate units. In an embodiment, two different half modules may fit into a single slot of a meter.

Figure 3A:
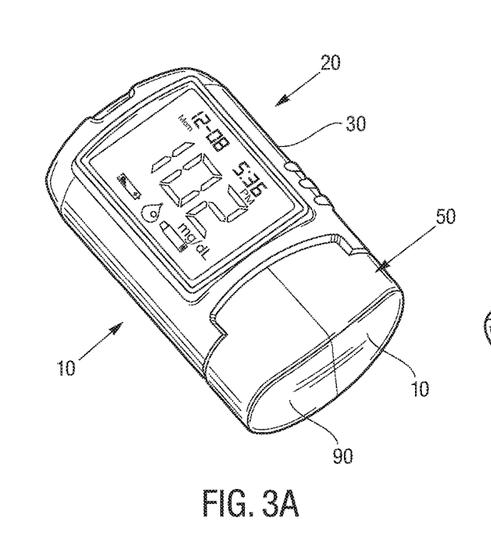
FIG. 3A is a perspective view of a meter and a module inserted therein, wherein the module is a split lancing device module. Half the module is for lancet storage and the other half of the module is the lancing device.
Figure 3B:
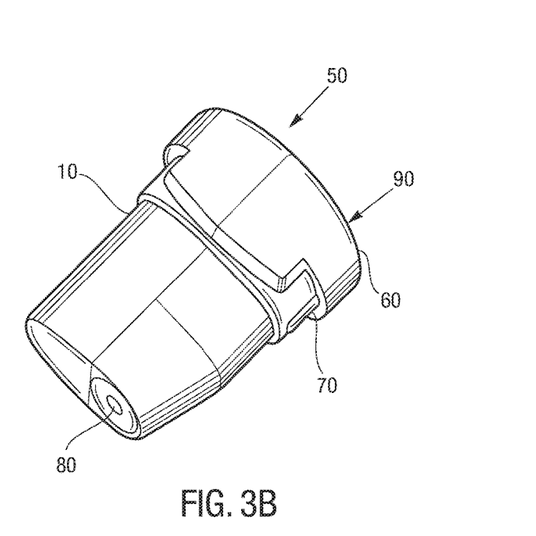
FIG. 3B is a perspective view of the split lancing device of FIG. 3A.

FIG. 3A is a perspective view of a meter 20 and a module 50 inserted therein, wherein the module 50 is an embodiment of a split module. In FIG. 3A, the split module is a split lancing device module. FIG. 3B is a perspective view of the split lancing device module of FIG. 3A. The split lancing device module of FIG. 3B includes a lancing device 90 and a lancet storage 100 that serves as a storage container for the lancets. Thus, part of the module may be for lancet storage and the other part of the module may be the lancing device. The parts may be the same or different sizes. The split lancing device module may be an integrated unit or it may be two units that can be separated when removed from the meter. Also, one of the two units may be separated from the meter while the other one remains in the slot in the meter. The split lancing device module may be configured to function while inserted in the meter or when one or both parts are removed from the meter. The lancing device includes a button to press to fire the lancet. Also, the lancing device includes a lance area and depth setting adjustment. Also, there is an opening at the top of the module.

FIGS. 4A-10B are embodiments showing active modules.

Figure 4A:
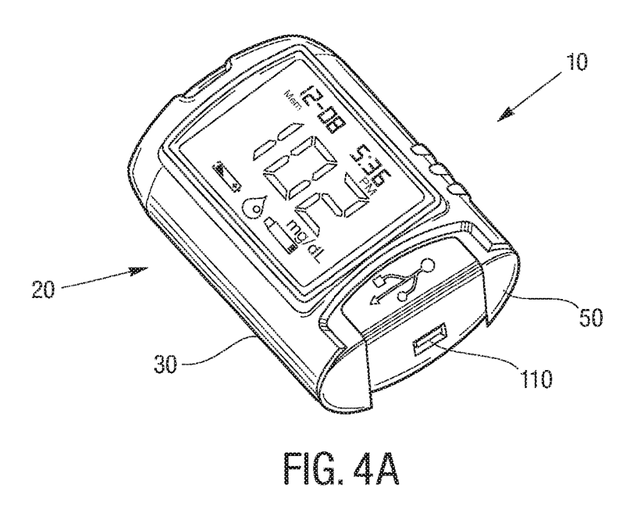
FIG. 4A is a perspective view of a meter and a module inserted therein, wherein the module is a USB module.
Figure 4B:
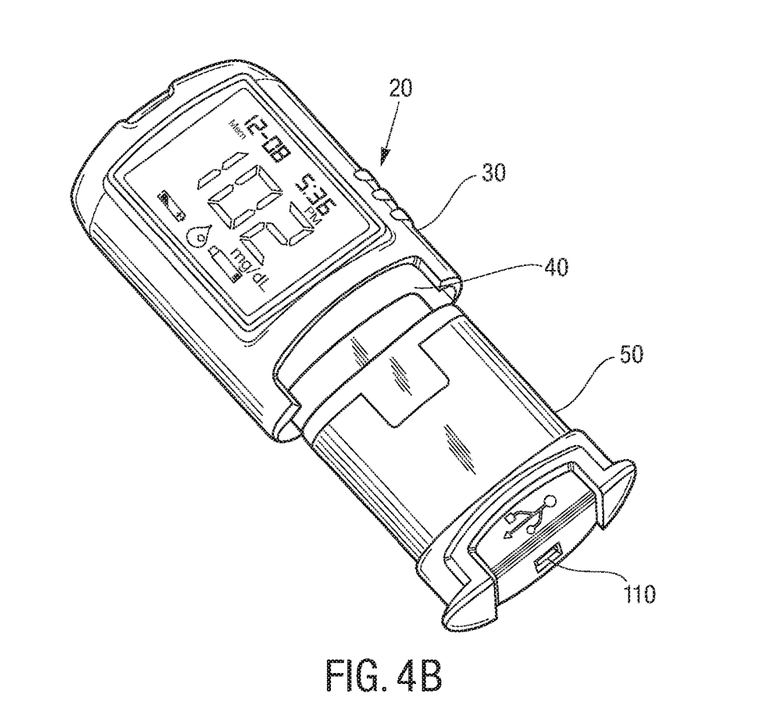
FIG. 4B is a perspective view of the meter and the USB module of FIG. 4A.

FIG. 4A is a perspective view of a meter 20 and a module 50 inserted therein, wherein the module 50 is a USB module. FIG. 4B is a perspective view of the meter 20 and the USB module of FIG. 4A. The module 50 may slide in and out of the meter 20. Also, the module 50 may lock in place inside the meter 20 to releasably secure the module 50 in the meter 20. The module 50 may be removed from the meter 20 and replaced by a different module. A USB module is a module 50 that when inserted into the meter allows for connectivity via a USB connection for downloading data to an external device such as a computer or other device. The USB module may include a port 110 for a USB cable or USB drive used to store data. In an embodiment, a diagnostic meter system includes a meter and USB module. The system may or may not include a USB cable. The USB cable may be an off-the-shelf USB. The USB cable, if present, can connect to another device, such as a computing device, to enable wired communication between the USB module and the computing device.

Another example of an active module is a wireless connection module. A wireless connection module is any module that can be inserted into the meter and enable the meter to connect wirelessly through any suitable means including, for example, GSM, radio frequency (RF), such as WiFi, Bluetooth®, Bluetooth Smart®, ANT/ANT+®, ZigBee®, cellular, Near Field Communication (NFC), optical (e.g., barcode, IRDA, OCR, or similar devices), sound (e.g., ultrasonic, subsonic/vibratory, or similar sounds), magnetic, thermal, electrical (e.g., resistance, impedance, voltage, current) or similar channels. In an embodiment, the wireless connection module includes a LED light or other indicator to show wireless connectivity.

Figure 5A:
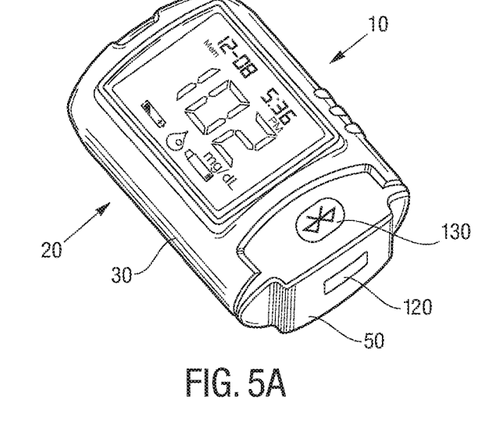
FIG. 5A is a perspective view of a meter and a module inserted therein, wherein the module is a Bluetooth module.
Figure 5B:
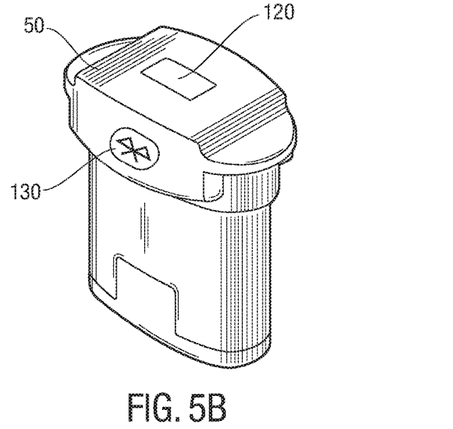
FIG. 5B is a perspective view of the Bluetooth module of FIG. 5A.

FIG. 5A is a perspective view of a meter 20 and a module 50 inserted therein, wherein the module 50 is a Bluetooth module. FIG. 5B is a perspective view of the Bluetooth module of FIG. 5A. The Bluetooth module may include a button 120 to launch appropriate software to download data from the meter 20 to a computer. For example, a button on the Bluetooth module may launch diabetes software, or other appropriate software, and start to download results into a data management system on a computer. The Bluetooth module shown in FIG. 5B includes a LED light 130 to indicate that the Bluetooth module is wirelessly connected to a computer.

Figure 6A:
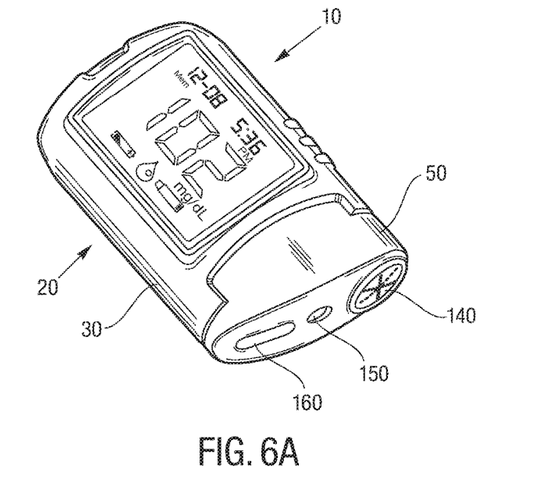
FIG. 6A is a perspective view of a meter and a module inserted therein, wherein the module is an audio module.
Figure 6B:
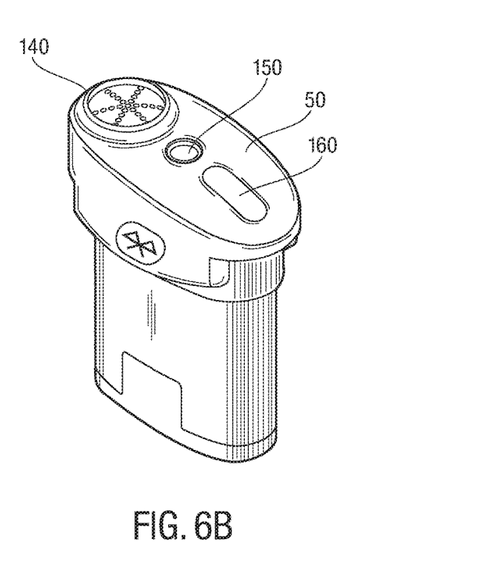
FIG. 6B is a perspective view of the audio module of FIG. 6A.

FIG. 6A is a perspective view of a meter 20 and a module 50 inserted therein, wherein the module 50 is an audio module. FIG. 6B is a perspective view of the audio module of FIG. 6A.

An audio module can be inserted into the meter 20 that would enable the meter 20 to enunciate the information shown on the display through a speaker 140 or an earphone. In addition, the audio module may be used to record information. For example, a user may speak into a microphone on the audio module to record information regarding a blood glucose reading. Such module also may include a headphone jack 150. A user may plug an earphone into the headphone jack and listen to instructions or hear results. The headphone may also include a microphone for the user to record information. In an embodiment shown in FIG. 6B, the audio module includes a speaker 140, a headphone jack 150, and a button 160 to press to hear diagnostic results such as a glucose result. An audio module may include at least one or any combination of features including a headphone jack, a speaker, a microphone, a button to hear meter readings or record results, and any other features that would enable a user to record audio or listen to audio from the meter. The audio module may include multiple buttons. A button may be included to repeat meter commands or results. In an embodiment, a meter system or kit includes a meter, an audio module, and earphones.

Figure 7A:
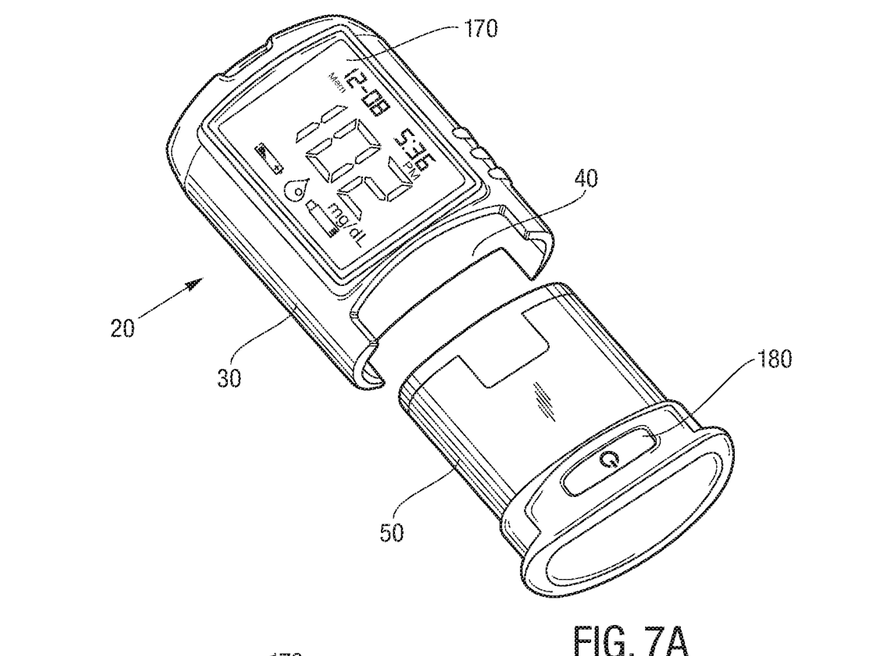
FIG. 7A is a perspective view of a meter and a module, wherein the module is a backlight module.
Figure 7B:
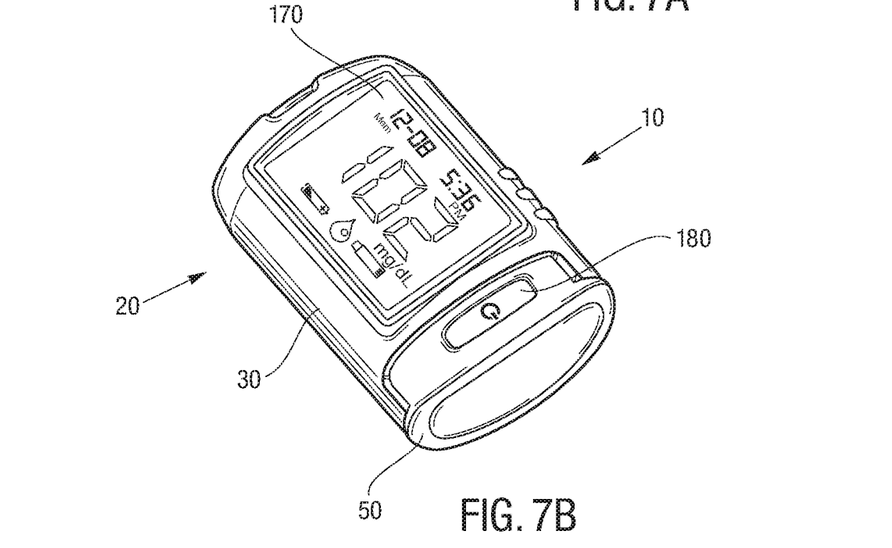
FIG. 7B is a perspective view of the meter of FIG. 7A with the backlight module inserted therein.

FIG. 7A is a perspective view of a meter 20 and a module 50, wherein the module 50 is a backlight module. The module 50 may slide in and out of the meter 20. Also, the module 50 may lock in place inside the meter 20. FIG. 7B is a perspective view of the meter of FIG. 7A with the backlight module inserted therein. The module 50 slides into the meter 20 and is locked in place to releasably secure the module 50 in the meter 20. The module 50 may be removed from the meter 20 and replaced by a different module. The module may be configured to provide backlighting to a display 170 on the meter or to illuminate a strip insertion area of the meter. The backlight module may include a button 180 to turn the backlight on and off. In an embodiment, the backlight module may use its own batteries rather than relying on the meter battery.

Figure 8A:
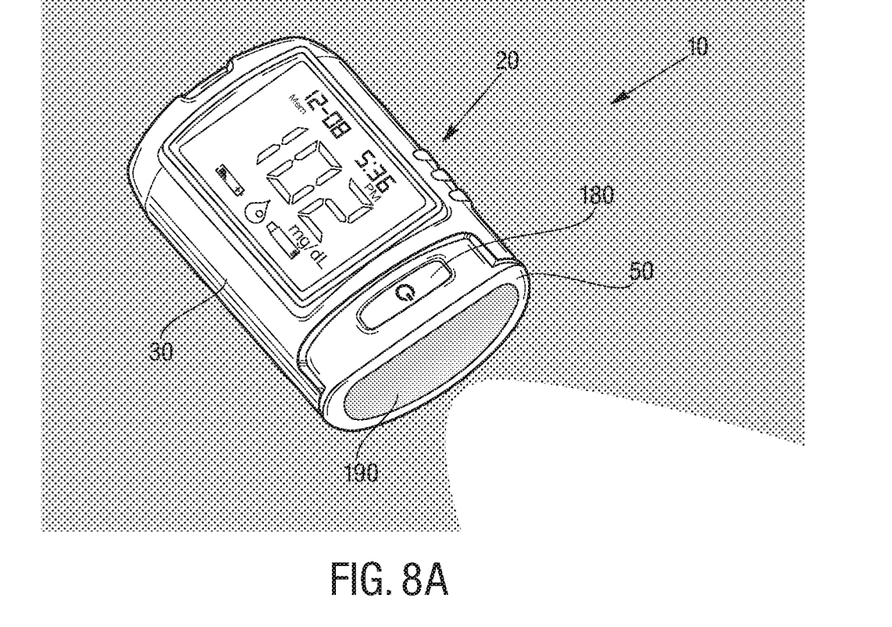
FIG. 8A is a perspective view of a meter and a module inserted therein, wherein the module is a flashlight module.
Figure 8B:
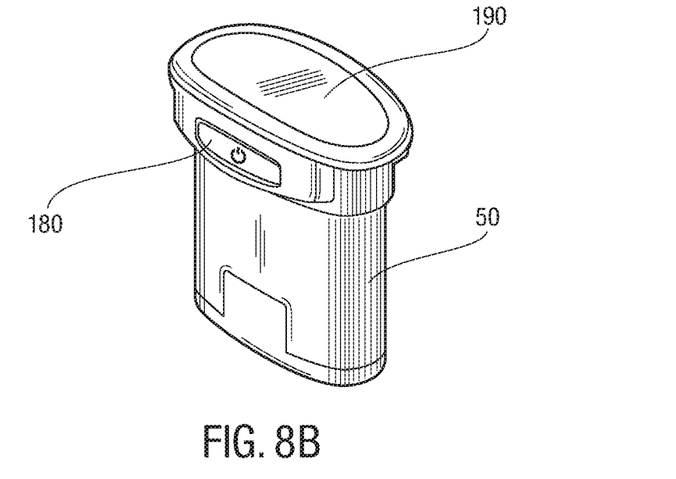
FIG. 8B is a perspective view of the flashlight module of FIG. 8A.

FIG. 8A is a perspective view of a meter 20 and a module 50 inserted therein, wherein the module 50 is a flashlight module. FIG. 8B is a perspective view of the flashlight module of FIG. 8A. A module 50 can be inserted that can function as a flashlight 190 to illuminate the testing area by emitting a light for testing in low light conditions. A flashlight module may include one or more batteries and, thus, not need to rely on the meter battery.

Combination modules may also be created which include two or more modules. The combination module may include passive modules, active modules, or a combination thereof. In an embodiment, a combination module is a flashlight combined with display backlighting. Another example of a combination module includes a Bluetooth module and a scanner such as a barcode scanner.

A module may be a multi-function or a combination module which has more than one feature or function within the same module. The multi-function module may include the features or functions of the passive modules and the active modules described herein, or a combination thereof. In an embodiment, the multi-function module includes two features. In an embodiment, the multi-function module includes more than two features.

Figure 9A:
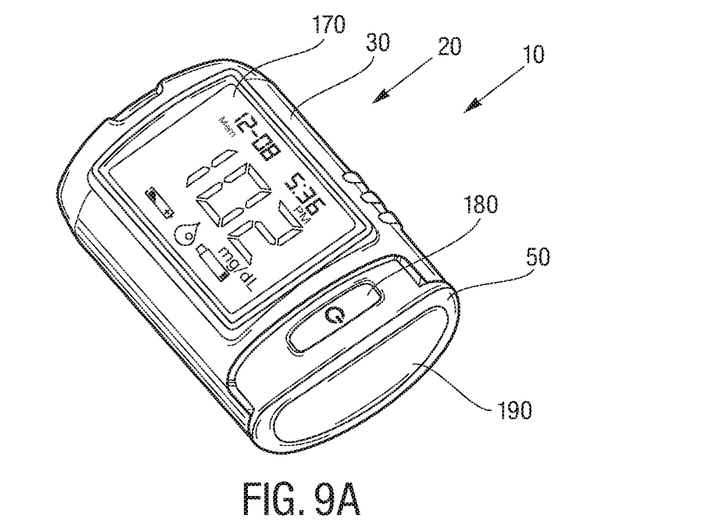
FIG. 9A is a perspective view of a meter and a multi-function module inserted therein, wherein the multi-function module is a flashlight/backlight module.
Figure 9B:
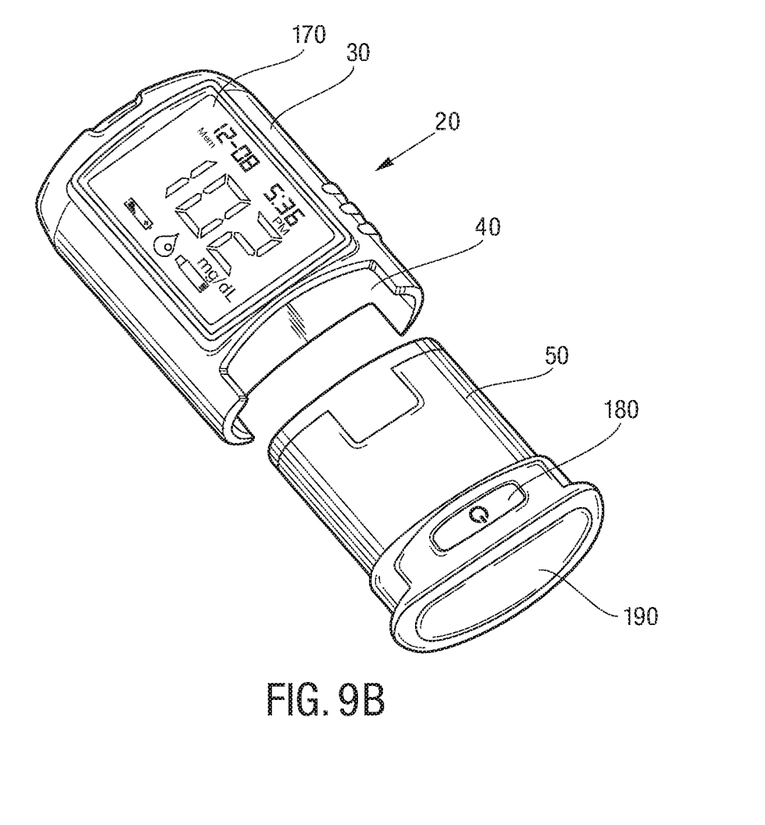
FIG. 9B is a perspective view of the meter and the multi-function module of FIG. 9A.

FIG. 9A is a perspective view of an embodiment of a meter 20 and a module 50 that is a multi-function module inserted therein, wherein the multi-function module includes two active module features. In particular, the multi-function module of FIG. 9A is a flashlight/backlight module to emit light. FIG. 9B is a perspective view of the meter 20 and the multi-function module of FIG. 9A. The flashlight/backlight module may include its own batteries so that it may not have to rely on the meter battery. Also, the flashlight/backlight module may be removed from the module and function as a stand alone flashlight 190. The multi-function module may slide in and out of the meter 20. Also, the multi-function module may lock in place inside the meter 20 to releasably secure the multi-function module in the meter 20. The multi-function module may be removed from the meter 20 and replaced by a different module.

Figure 10A:
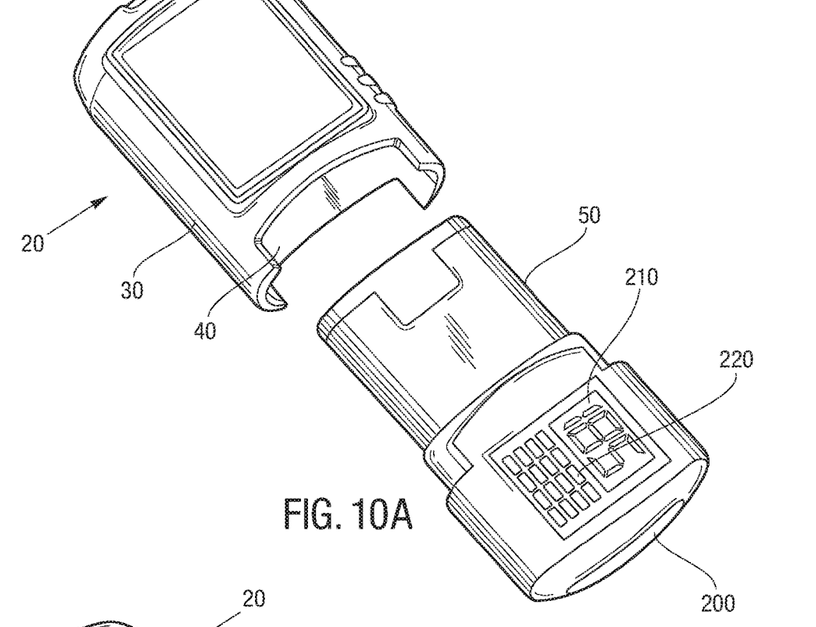
FIG. 10A is a perspective view of a meter and a multi-function module, wherein the multi-function module includes a carbohydrate counter and barcode scanner.
Figure 10B:
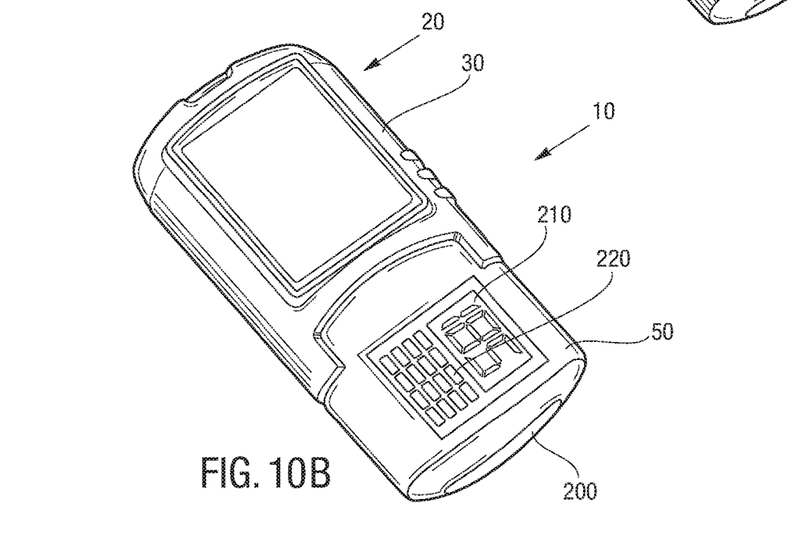
FIG. 10B is a perspective view of the meter of FIG. 10A with the multi-function module inserted therein.

FIG. 10A is a perspective view of an embodiment of a meter 20 and a module 50 that is a multi-function module which includes two active module features. The module 50 may slide in and out of the meter 20. Also, the module 50 may lock in place inside the meter 20 to releasably secure the module 50 in the meter 20. The module 50 may be removed from the meter 20 and replaced by a different module. The multi-function module of the embodiment of FIG. 10A includes a carbohydrate counter and a scanner 200, such as a barcode scanner. In an embodiment, the module 50 may include an insulin bolus calculator. FIG. 10B is a perspective view of the meter 20 of FIG. 10A with the multi-function module inserted into the meter 20. The scanner may be placed at the end of the module 50 or any other suitable location. In FIG. 10A and FIG. 10B, the scanner 200 is situated at the end of the module so that it is exposed when the module 50 is inserted in the slot 40 in the housing 30 of the meter 20. The carbohydrate counter may calculate planned carbohydrate intake. Also, the scanner may be used to scan food packages and automatically input carbohydrate information, or other nutritional information, into the meter. In an embodiment of a blood glucose meter, the meter may suggest an insulin bolus based on the last glucose result. The scanner may be used in a hospital or other healthcare facility to scan patient information such as identification bracelets and vials of test strips or other test media. In addition, a wireless connection module used with a scanner such as a barcode scanner can transmit information to hospital computers.

In an embodiment, a module can be inserted into the meter that could function as a carbohydrate counter and a total carbohydrate calculator. The module may include a small LCD screen 210 and one or more buttons and/or a full numeric keypad 220 to input the amounts. The module may also contain carbohydrate information of common foods to allow the user to look up and select the appropriate values.

In an embodiment, the meter has a slot for receiving a module extender. The module extender may be a module having at least two features or functions as described herein with respect to passive and active modules. The features may be active or passive or a combination thereof. The module extender may be an additional active or passive module that is attached to another module in the meter that is an active or passive module. For example, the module extender may be an active module that connects to a passive module in the meter, such as a Bluetooth module that includes a strip vial holder. The module in the meter may be an active module that includes an adapter connection for another active module or module extender, such as a backlight module that includes a port for any other active (or passive) module.

FIGS. 11A-12C show embodiments of diagnostic meters and systems including module extenders.

Figure 11A:
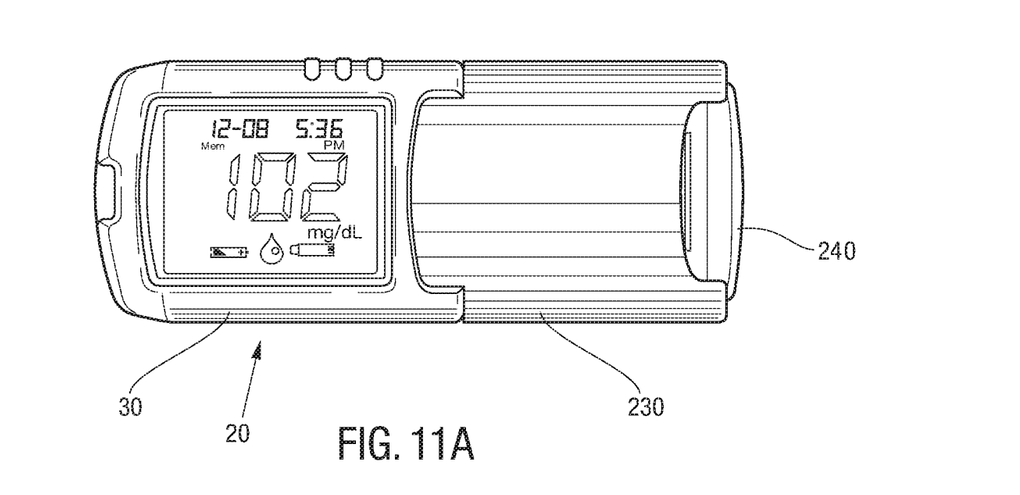
FIG. 11A is a perspective view of a meter with a module extender attached to a module (not shown) inserted in the meter, where the meter and module extender are the same color.
Figure 11B:
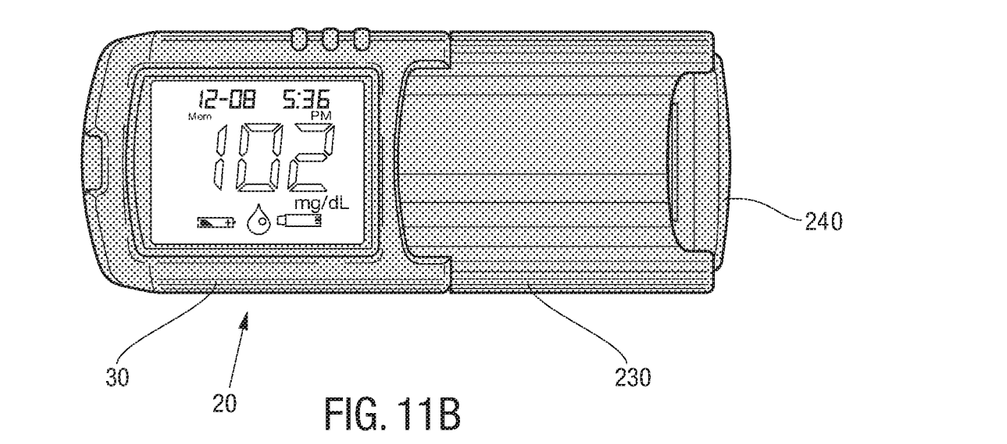
FIG. 11B is a perspective view of a meter with a module extender attached to a module (not shown) inserted in the meter, where the meter and module extender are different colors.

FIG. 11A is a perspective view of a meter 20 with a module extender 230 attached to a module (not shown)

inserted in the meter, where the meter 20 and module extender 230 may have the same color or pattern. FIG. 11B is a perspective view of a meter 20 with a module extender 230 attached to a module (not shown) inserted in the meter, where the meter 20 and module extender 230 may be different colors or patterns. Also shown in FIGS. 11A and 11B is a second module 240 inserted into the module extender 230. In an embodiment, a module extender acts as an adapter to secure the first module that is inserted into the slot in the housing of the meter to a second module.

As discussed above, the module extender may include two modules in an integrated structure or the module extender may be a second module or encompass a second module removably connected to a first module where one or both modules extend into the slot of the meter.

In an embodiment, the module extender is a wireless connection module, such as a Bluetooth module, and the module extender is a vial for storing test strips.

The module extender may be two or more modules integrated into a single unit that is insertable in the slot of a meter. In an embodiment, the module extender that is attached to a module is configured to have at least a portion of a module inserted into a slot in a meter. Thus, the module extender may include two or more separate modules where a first module is inserted into a meter and a second module is attached to the first module. The module extender may slide over or under the first module such that, in use, the first module and second module are both inserted into the slot of the meter. At least a portion of the first module and/or the second module may be inserted into the slot to any desired depth up to the depth of the slot.

Figures 12A, 12B, 12C:
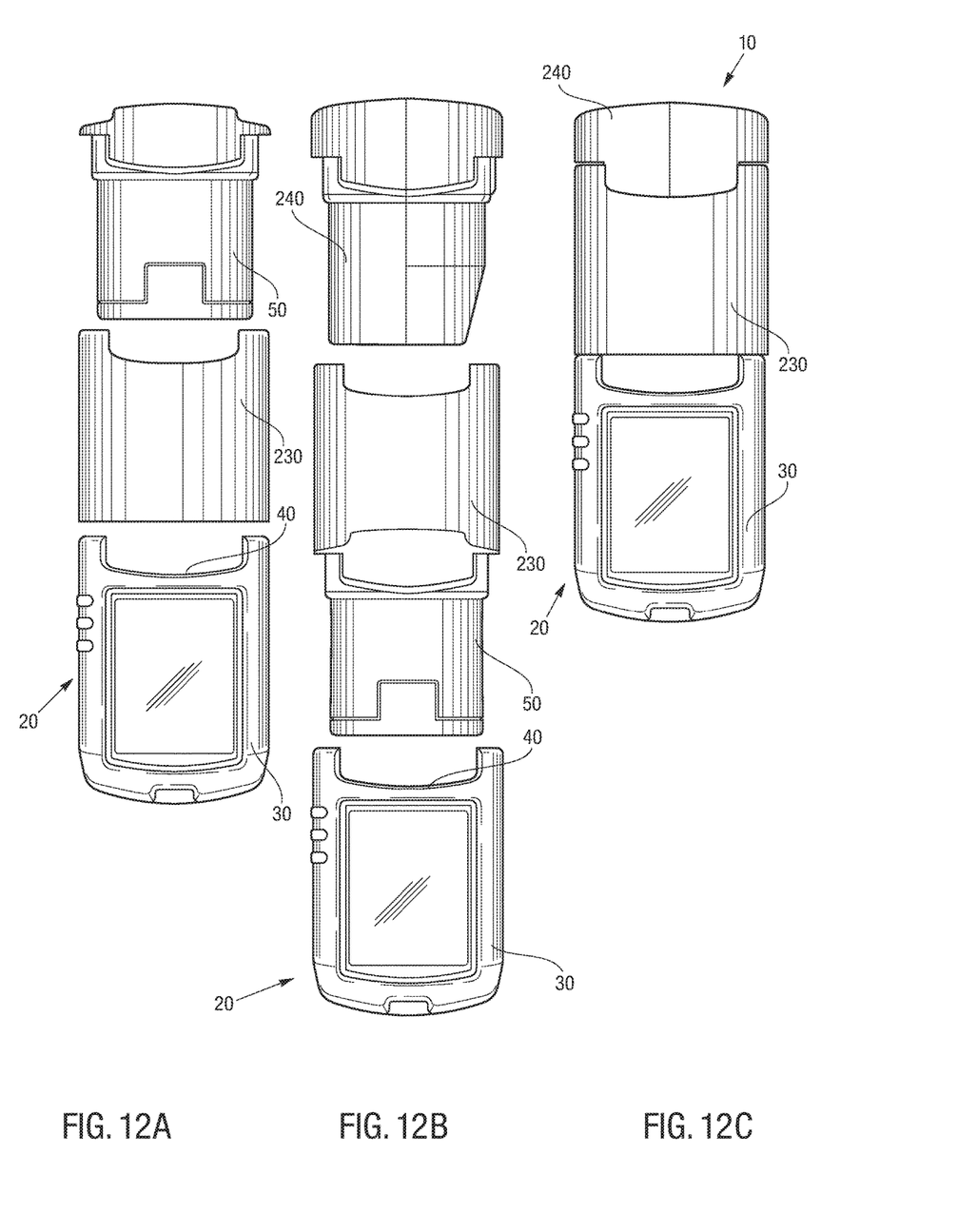
FIG. 12A is a side view of a meter, and an active module inserted into a module extender.
FIG. 12B is a side view of a meter with the active module passed through the module extender of FIG. 12A and locked into place.
FIG. 12C is a side view of a meter with the active module and the module extender of FIG. 12B inserted into the meter, and a passive module inserted into the module extender.

FIGS. 12A, 12B, and 12C show an embodiment of a module extender 230 connected to a first module 50 such as an active module and inserted into a meter 20. FIG. 12A is a side view of the meter 20, and the first module 50 inserted into the module extender 230. The first module 50 may slide in and out of the meter 20. Also, the first module 50 may lock in place inside the meter 20 to releasably secure the first module 50 in the meter 20. The first module 50 may be removed from the meter 20 and replaced by a different module.

FIG. 12B is a side view of the meter 20 and the first module 50 passed through the module extender 230 of FIG. 12A and locked into place. FIG. 12B also shows a second module 240 such as a passive module that may be inserted into the module extender 230.

FIG. 12C shows the first module 50 and the module extender 230 of FIG. 12B inserted into the meter 20, with the second module 240 inserted into the module extender 230. The second module 240 may be a passive module such as a lancing device. The second module 240 may slide in and out of the module extender 230. Also, the second module 240 may lock in place inside the module extender 230 to releasably secure the second module 240 in the module extender 230. The second module 240 may be removed from the module extender 230 and replaced by a different module.

FIGS. 12A, 12B, and 12C show a method of having an active module slide through an module extender or adapter, but get retained by the module extender or adapter so that the active module does not completely pass through. The active module may be locked in place in the module extender or adapter to releasably secure the active module in the module extender or adapter. The active module may be removed from the module extender or adapter and replaced by a different module. The active module and module extender (or adapter) assembly slide into the meter. The active module and module extender assembly may be locked in place in the meter to releasably secure the active module and module extender assembly in the meter. Once the assembly is in place, a second module can slide into the module extender and connect to the assembly in any suitable manner including those set forth with respect to securing a first module to the meter. The second module may be locked into the module extender to releasably secure the second module in the module extender. One or more module extenders and one or more modules may be used to form the customizable meter.

In an embodiment, a diagnostic meter system includes a meter and at least one module as described above. In an embodiment, a diagnostic kit includes a meter and two or more modules that a user may interchangeably insert into a slot in the housing of a meter.

In an embodiment, a diagnostic meter system includes a meter as described above and one or more modules. In an embodiment, a diagnostic meter system includes a plurality of modules. The plurality of modules may include a module blank which does not have a function but is a placeholder when a module having a function is not inserted in the slot. In an embodiment, the meter will function without a module or module blank in the slot.

In use, a user may insert a desired module into a slot in the housing of a diagnostic meter. In particular, at least a portion of the module will be inserted into the slot. The module will be secured in the slot by any suitable mechanism. The user may know when the module is secured when the module clicks in place. To release the module, the user may either pull the module out of the slot or release it from the slot. In an embodiment, the module will have a button to press to release the module from the meter. Users may hot swap different modules to perform different desired functions. In an embodiment, the user may remove the backlight module after testing to insert a Bluetooth module to transfer test results to a cell phone without needing to turn off the device.

The diagnostic meters, systems, and kits described in this disclosure allow users to customize their device hardware to suit their needs. Also, the diagnostic meters described herein extend the life of a diagnostic meter by retaining a common core device (the meter) and adding features by swapping in different modules. Thus, the meters and systems described herein allow users to take advantage of new features as they become available without having to purchase a new meter. Users may only purchase modules having desired features.

In an embodiment, a customizable diagnostic meter is provided. The customizable diagnostic meter includes a meter, such as a portable meter for performing a diagnostic test. The meter includes a housing having at least one slot, and a module having one or more functions. The slot is configured to receive and removably secure at least a portion of a module.

In an embodiment, a customizable diagnostic meter includes a meter, such as a portable meter, for performing a diagnostic test, wherein the meter includes a housing having at least one slot. The diagnostic meter also includes a first module having one or more functions, wherein the slot is configured to receive and removably secure at least a portion of the first module; and a second module having one or more functions, wherein the second module is configured for removable attachment to at least a portion of the first module.

In an embodiment, a customizable diagnostic meter kit is provided. The kit includes a meter for performing a diagnostic test, wherein the meter includes a housing having at least one slot. The kit also includes two or more modules, wherein each module has one or more functions and the module has a portion that is configured to be inserted and removably secured in the slot. The kit may also include one or more module extenders.

All patents, patent applications, and published references cited herein are hereby incorporated by reference in their entirety. It will be appreciated that several of the above-disclosed and other features and functions, or alternatives thereof, may be desirably combined into many other different systems or application. Various alternatives, modifications, variations, or improvements therein may be subsequently made by those skilled in the art.

What is claimed is:

1. A customizable diagnostic meter comprising:
a meter for performing a diagnostic test of an analyte in a sample applied to a test strip, the meter comprising a housing having at least one slot and a test strip port configured to receive the test strip; and
a module having one or more functions relating to the diagnostic test of the analyte; and
a module extender connected to the module and configured to act as an adapter to removably couple one or more additional modules to the meter, the additional modules having one or more functions relating to the diagnostic test of the analyte,
wherein the at least one slot is configured to receive and removably secure at least a portion of a module,
wherein the module comprises a wireless connection module including a Bluetooth or WiFi connection.

2. The meter of claim 1, wherein the meter is a blood glucose meter.

3. The meter of claim 1, wherein the meter is portable.

4. The meter of claim 1, wherein the module is a passive module.

5. The meter of claim 1, wherein the module is an active module.

6. The meter of claim 1, wherein the module is a portable vial, a lancing device, a USB module, a wireless connection module, an audio module, a backlight module, a flashlight, a carbohydrate counter, an insulin bolus calculator, or a scanner, or a combination thereof.

7. The meter of claim 1, wherein the module is a multi-function module.

8. The meter of claim 7, wherein the multi-function module includes a carbohydrate counter and a scanner.

9. The meter of claim 1, wherein the module extender includes a flashlight and a backlight.

10. A customizable diagnostic meter comprising:
a meter for performing a diagnostic test of an analyte in a sample applied to a test strip, the meter comprising a housing having at least one slot and a test strip port configured to receive the test strip;
a first module having one or more functions relating to the diagnostic test of the analyte, wherein the at least one slot is configured to receive and removably secure at least a portion of the first module;
a second module having one or more functions relating to the diagnostic test of the analyte, the second module configured for removable attachment to at least a portion of the first module; and
a module extender connected to a first module or a second module and configured to act as an adapter to removably couple one or more additional modules to the meter, the one or more additional modules having functions relating to the diagnostic test of the analyte,
wherein at least one of the first or second modules comprises a wireless connection module including a Bluetooth or WiFi connection.

11. The meter of claim 10, wherein the first module is different than the second module.

12. The meter of claim 11, wherein the first module and the second module are selected from the group consisting of: a portable vial, a lancing device, a USB module, a wireless connection module, an audio module, a backlight module, a flashlight, carbohydrate counter, insulin bolus calculator, and a scanner.

13. The meter of claim 10, wherein the meter is portable.

14. The meter of claim 10, wherein the module extender includes a flashlight and a backlight.

15. A customizable diagnostic meter kit comprising:
a meter for performing a diagnostic test of an analyte in a sample applied to a test strip, the meter comprising a housing having at least one slot and a test strip port configured to receive the test strip; and
two or more modules, wherein each module has one or more functions and a portion that is configured to be inserted and removably secured in the at least one slot; and
a module extender connectable to one of the two or more modules and configured to act as an adapter to removably couple one or more additional modules to the meter, the additional modules having functions relating to the diagnostic test of the analyte,
wherein at least one of the functions of the two or more modules relates to the diagnostic test of the analyte,
wherein at least one of the two or more modules comprises a wireless connection module including a Bluetooth or WiFi connection.

16. The kit of claim 15, wherein the portions of the two or more module configured for insertion in the at least one slot are of the same size and shape.

17. The kit of claim 15, wherein at least one module is a portable vial, a lancing device, a USB module, a wireless connection module, an audio module, a backlight module, a flashlight, a carbohydrate counter, an insulin bolus calculator, or a scanner.

18. The kit of claim 15, wherein one module is a USB module, and the kit further includes a USB cable.

19. The meter of claim 15, wherein the module extender includes a flashlight and a backlight.

20. A customizable diagnostic meter comprising:
a meter for performing a diagnostic test of an analyte in a sample applied to a test strip, the meter comprising a housing having at least one slot and a test strip port configured to receive the test strip;
a module having one or more functions relating to the diagnostic test of the analyte, the module comprising a wireless connection module including a Bluetooth or WiFi connection; and
a module extender connected to the module and configured to act as an adapter to removably couple one or more additional modules to the meter, the additional modules having one or more functions relating to the diagnostic test of the analyte,
wherein the at least one slot is configured to receive and removably secure at least a portion of a module.

21. The meter of claim 20, wherein the module extender includes a flashlight and a backlight.

* * * * *